United States Patent
Bergman et al.

(10) Patent No.: US 9,414,746 B2
(45) Date of Patent: Aug. 16, 2016

(54) EYE TRACKING

(75) Inventors: Janne Bergman, Tampere (FI); Jari Saukko, Tampere (FI); Jussi Severi Uusitalo, Hameenlinna (FI)

(73) Assignee: Nokia Technologies Oy, Espoo (FI)

( * ) Notice: Subject to any disclaimer, the term of this patent is extended or adjusted under 35 U.S.C. 154(b) by 9 days.

(21) Appl. No.: 14/365,176

(22) PCT Filed: Jan. 26, 2012

(86) PCT No.: PCT/FI2012/050071
§ 371 (c)(1),
(2), (4) Date: Oct. 1, 2014

(87) PCT Pub. No.: WO2013/110846
PCT Pub. Date: Aug. 1, 2013

(65) Prior Publication Data
US 2015/0015847 A1 Jan. 15, 2015

(51) Int. Cl.
| A61B 3/14 | (2006.01) |
| A61B 3/113 | (2006.01) |
| G06F 3/01 | (2006.01) |
| G02C 11/00 | (2006.01) |
| G06F 3/041 | (2006.01) |

(52) U.S. Cl.
CPC ............. *A61B 3/113* (2013.01); *G02C 11/10* (2013.01); *G06F 3/013* (2013.01); *G06F 3/041* (2013.01)

(58) Field of Classification Search
CPC .............................. A61B 3/113; G02C 11/10
USPC .......................................... 351/158, 209, 210
See application file for complete search history.

(56) References Cited

U.S. PATENT DOCUMENTS

| 5,726,916 A | 3/1998 | Smyth | |
| 8,184,067 B1 * | 5/2012 | Braun | G09G 5/00 345/7 |
| 8,398,239 B2 * | 3/2013 | Horning | G02B 27/017 351/209 |
| 2005/0099601 A1 | 5/2005 | MacDougall et al. | |
| 2006/0115130 A1 | 6/2006 | Kozlay | |
| 2010/0033196 A1 * | 2/2010 | Hayakawa | G01B 7/22 324/686 |
| 2010/0045932 A1 | 2/2010 | Shelhamer et al. | |

FOREIGN PATENT DOCUMENTS

| JP | 2009291391 | 12/2009 |
| WO | WO9113584 | 9/1991 |
| WO | WO2011100436 | 8/2011 |
| WO | WO2011/153158 | 12/2011 |

OTHER PUBLICATIONS

International Search Report for International Application No. PCT/FI2012/050071—Date of Completion of Search: Nov. 16, 2012—5 pages.

(Continued)

*Primary Examiner* — Huy K Mai
(74) *Attorney, Agent, or Firm* — Locke Lord LLP

(57) ABSTRACT

An apparatus (100), comprising a transparent capacitive sensor (102); a body (101) configured to support the transparent capacitive sensor in front of an eye (112) of a user (110); and a driver (106) configured to receive signals from the sensor and to determine eye movements based on the received signals, wherein the sensor (102) is configured to detect movement of the eye (112) based on electrostatic effect caused by a bulge of the cornea of the eye (112). The apparatus may be wearable by the user like eyeglasses.

21 Claims, 3 Drawing Sheets

(56) References Cited

OTHER PUBLICATIONS

PCT Written Opinion of the International Searching Authority for International Application No. PCT/FI2012/050071—Date of Completion of Search: Nov. 16, 2012—5 pages.

English Language Abstract of Japanese Patent Application Publication No. JP2009291391, 1 page.
English Language Machine Translation of Japanese Patent Application Publication No. JP2009291391, 11 pages.
Extended European Search Report for EP Application No. 12866908.2—Date of Completion of Search: Aug. 12, 2015, 6 pages.

* cited by examiner

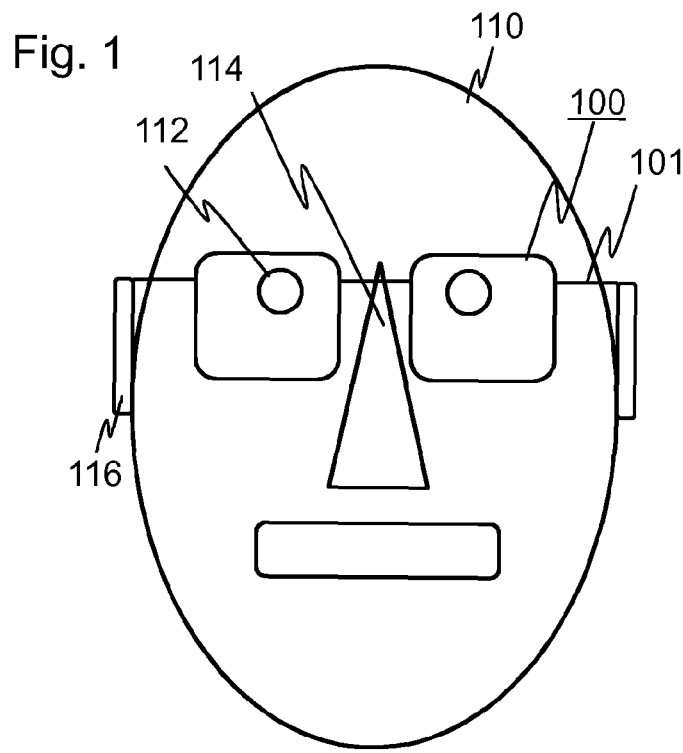
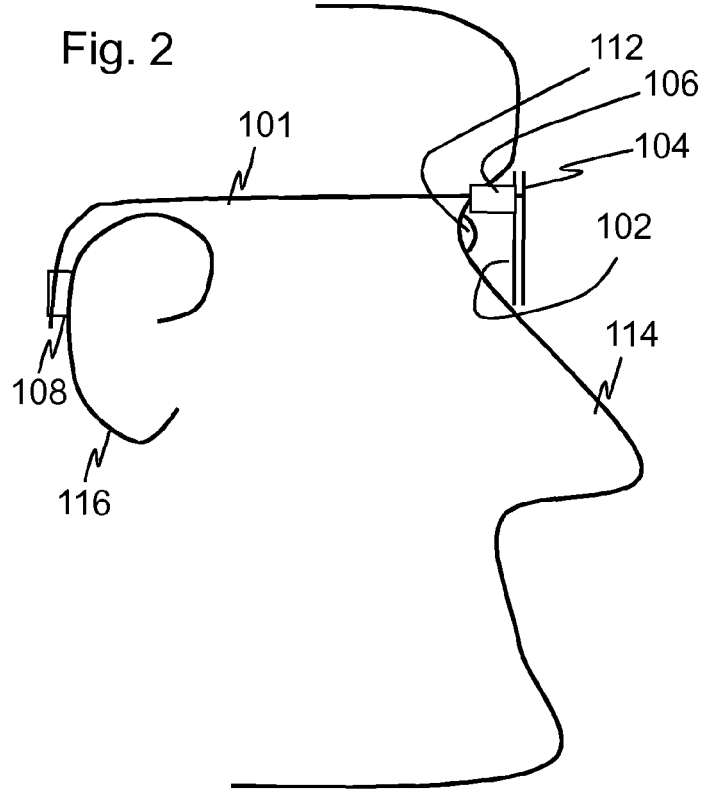

EYE TRACKING

TECHNICAL FIELD

The present application generally relates to eye tracking. In particular, though not exclusively, the present application relates to contactless eye tracking.

BACKGROUND

Eyes of human beings move for various reasons. There are voluntary movements and involuntary movements. The tracking of the eye movements has various applications such as detecting drowsiness of drivers.

Eye tracking devices are often divided into contacting and contactless devices. There are devices that look into the eye using a camera system and deduce eye movements from optical signals. There are also devices in which a sensor is attached to the eye like a contact lens, or in which electric changes about the eye are measured with pads connected to the skin around the eye.

SUMMARY

Various aspects of examples of the invention are set out in the claims.

According to a first example aspect of the present invention, there is provided an apparatus comprising:
   transparent capacitive sensor;
   a body configured to support the transparent capacitive sensor in front of an eye of a user; and
   a driver configured to receive signals from the sensor and to determine eye movements based on the received signals.

The sensor may be configured to detect movement of the eye based on the electrostatic effect caused by the bulge of the cornea.

The apparatus may be wearable by the user. The apparatus may be wearable like eyeglasses.

The sensor may be made of transparent material.

The sensor may be formed in a sheet of transparent material. The sheet may also form the body.

The body may be supported by the nose of the user and/or by one or two ears of the user.

The sensor may be integrated with a lens of eyeglasses. Alternatively, the sensor may be attached to a lens of eyeglasses or to a frame of eyeglasses so that the sensor resides between the eye of the user and a lens of the eyeglasses, when the eyeglasses are worn by the user.

The sensor may be attached to a display of video glasses.

The sensor may be comprise transparent conductive material selected from a group consisting of: Indium Tin Oxide; Carbon nanotube based conductive coatings; films of graphene; thin metal films; inherently conductive polymers (ICPs); aluminum zinc oxide (AZO), gallium zinc oxide (GZO) or indium zinc oxide (IZO).

The sensor may be covered by a protective coating.

The sensor may comprise two layers of transparent conductive material sandwiching a layer of non-conductive material.

The sensor may be attached to a lens of eyeglasses by optical adhesive.

The apparatus may comprise a flexible printed circuit (FPC) configured to operatively connect the sensor to the driver.

The apparatus may comprise a printed wiring board (PWB) configured to operatively connect the sensor to the driver.

The apparatus may comprise a printed wiring board (PWB) configured to operatively connect the sensor to the driver.

The apparatus may comprise an analog-to-digital converter configured to convert analog signals produced by the sensor to digital signals.

The driver may comprise the analog-to-digital converter.

The flexible printed circuit may comprise the driver. Alternatively, the printed wiring board may comprise the driver.

The flexible printed circuit may comprise the analog-to-digital converter. Alternatively, the printed wiring board may comprise the analog-to-digital converter.

The apparatus may comprise a touch controller. The touch controller may be configured to detect touching of the user at one or more touch sensitive areas in the body and/or on the driver.

The apparatus may further comprise a heartbeat detector. The heartbeat detector may be integrated with or attached to the body. The heartbeat detector may be arranged behind an ear of the user when the apparatus is worn by the user.

The body may be formed of eyeglass frames.

The body may be configured to support the transparent capacitive sensor in front of the eye of a user at a proximate distance. The proximate distance may be such that the eyelash of the user does not reach to transparent materials in front of the eye. The proximate distance may be such that the eyebrow of the user does not reach to transparent materials in the visible field of the eye. The proximate distance may correspond to the distance of normal eyeglass lenses from eyes.

The apparatus may comprise two of the sensors. The apparatus may be configured support one of the sensors in front of each of two eyes of the user.

The apparatus may comprise a wired connection interface for connecting with an external device. The apparatus may be configured to provide the external device with eye tracking signals corresponding to the detected eye movements.

The apparatus may be configured to provide the external device with eye tracking signals corresponding to other sensory data collected by the apparatus, such as heartbeat information or touch information.

The wired connection interface may comply with a standard. The standard may be selected from a group consisting of Inter-Integrated Circuit (I2C) protocol, Serial Peripheral Interface (SPI), Universal serial bus (USB) and IEEE-1394.

The apparatus may be configured to receive operating power from the external device.

The apparatus may comprise a wireless connection interface for connecting with an external device. The wireless connection interface may comply with a standard. The standard may be selected from a group consisting of: low power Bluetooth, IEEE 802.11 (wireless LAN), ultra-wide band (UWB) radio link, and Infrared Data Association (IrDA) link.

According to a second example aspect of the present invention, there is provided a method comprising:
   supporting a transparent capacitive sensor in front of an eye of a user;
   sensing movement of the eye of the user by the transparent capacitive sensor and producing corresponding signals; and
   determining eye movements based on the produced signals.

According to a third example aspect of the present invention, there is provided a method comprising:
   receiving signals from a transparent capacitive sensor located in front of an eye of a user; and
   determining movement of the eye based on the received signals.

According to fourth example aspect of the present invention, there is provided a computer program, comprising:
  code for receiving signals from a transparent capacitive sensor located in front of an eye of a user; and
  code for determining movement of the eye based on the received signal
  when the computer program is run on a processor.

According to a fifth example aspect of the present invention, there is provided an apparatus comprising:
  means for transparent capacitive sensing;
  body means for supporting the means for transparent capacitive sensing in front of an eye of a user; and
  driver means for receiving signals from the transparent capacitive sensing means and for determining eye movements based on the received signals.

Any foregoing memory medium may comprise a digital data storage such as a data disc or diskette, optical storage, magnetic storage, holographic storage, opto-magnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device.

Different non-binding example aspects and embodiments of the present invention have been illustrated in the foregoing. The above embodiments are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which:

FIGS. 1 and 2 show a schematic drawing of a head-worn apparatus, when seen from front and side, respectively;

FIG. 5 shows equipment suited for illustration of a controller according to an example an example embodiment of.

DETAILED DESCRIPTION OF THE DRAWINGS

Figure 3:
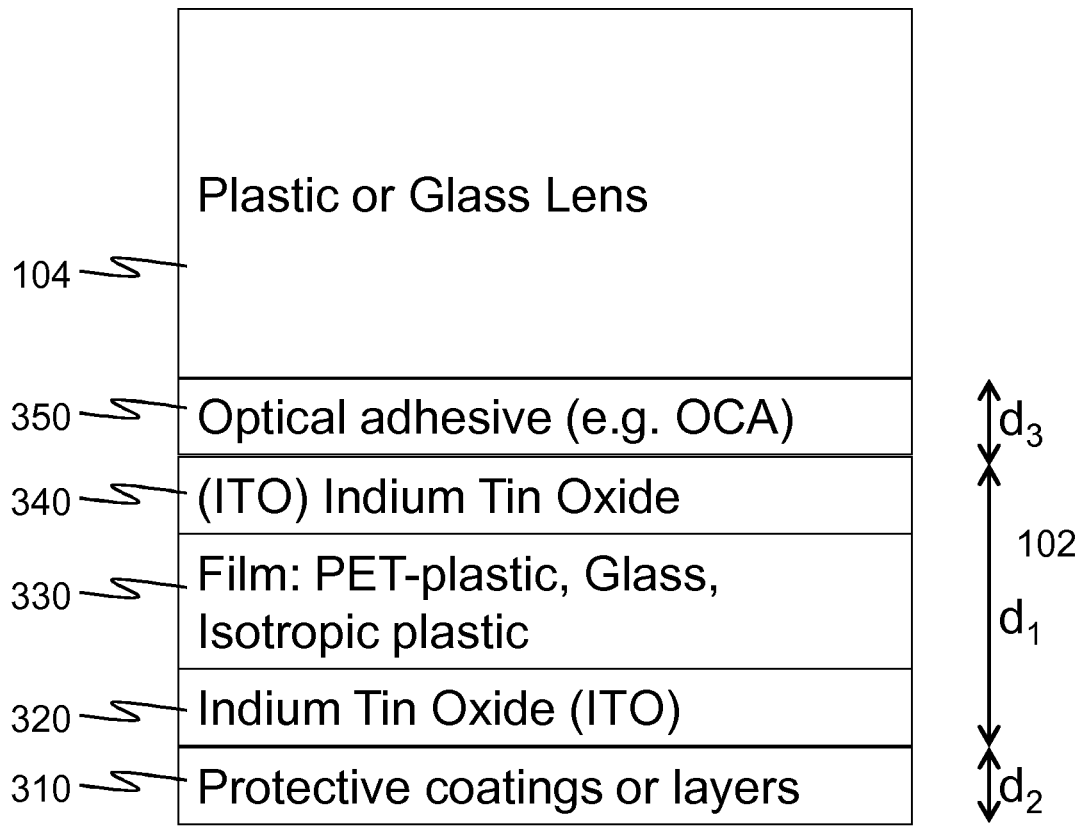
FIG. 3 is a schematic drawing of layers of a transparent capacitive sensor according to an example embodiment.
Figure 4:
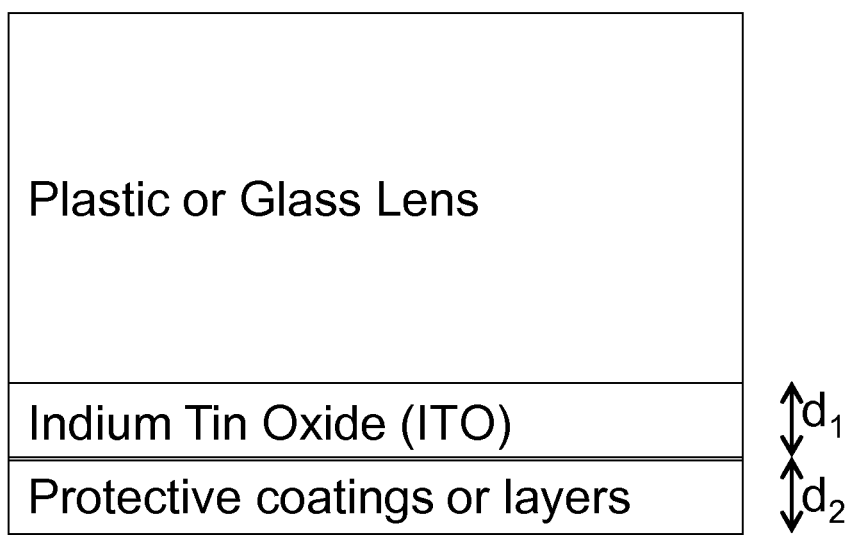
FIG. 4 is a schematic drawing of layers of a transparent capacitive sensor according to an example embodiment.

An example embodiment of the present invention and its potential advantages are understood by referring to FIGS. 1 through 6 of the drawings.

FIGS. 1 and 2 show a schematic drawing of a head-worn apparatus 100, when seen from front and side, respectively. The apparatus 100 comprises a transparent capacitive sensor 102 supported by a body 101 or frame in front of an eye 112 of a user 110. The apparatus 100 further comprises a driver 106 configured to receive signals from the sensor 102 and to determine eye movements based on the received signals.

It is known that the human eye has a bulge at the cornea. The sensor 102 can detect movement of the eye 112 based on the electrostatic effect caused by the bulge of the cornea of the eye 112.

The apparatus may be wearable by the user. The apparatus may be wearable like eyeglasses.

The sensor 102 of FIG. 2 is made of transparent conductive material so that the user 110 can see through the sensor 102. For instance, the sensor can be formed of a sheet of transparent conductive material. In an example embodiment, unlike in FIGS. 1 and 2, the sheet also forms the body 101. Such a sheet can be attached to the head e.g. by adhesive material such as glue or tape or by forming it suitably to conform to the shapes of the head so that the sheet attaches to the head sufficiently to remain in place at least when the user 110 remains still.

In an example embodiment and in FIG. 2, the body 101 is supported by the nose 114 of the user and/or by one or two ears 116 of the user.

In an example embodiment and in FIG. 2, the sensor is attached to a lens or to the frame of eyeglasses so that the sensor 102 resides between the eye of the user and a lens of the eyeglasses, when the eyeglasses are worn by the user. In an alternate example embodiment, the sensor is integrated with a lens of eyeglasses.

In an example embodiment and in FIG. 3, the sensor 102 is adhesively attached to a lens of eyeglasses on the side towards the eye. In such a case, the user watches through a series of adjacent optically transparent layers of: protective coatings or layers 310 of thickness $d_2$ (e.g. 0.05 mm), a first conductive transparent layer 320, an insulating layer 330 such as a film of polyethylene terephthalate (PET), glass or isotropic plastics material and a second conductive transparent layer 340. The first and second transparent conductive layers 320, 340 and the insulating layer 330 together form a sensor 102 of an example embodiment. The thickness of such a sensor 102 is marked in FIG. 3 as $d_1$ that is, for instance, 0.1 mm to 0.125 mm thick. Further, FIG. 3 shows an optical adhesive layer 350 of, for instance, optically clear adhesive (OCA) of thickness $d_3$ that is, for example, 0.05 mm to 0.1 mm thick. Behind the adhesive layer 350, FIG. 3 shows the lens of the eyeglasses 104. It is understood that through this description the presented examples of thicknesses and compositions of various layers merely represent particular example embodiments.

In an example embodiment, the transparent conductive material is selected from a group consisting of: Indium Tin Oxide; Carbon nanotube based conductive coatings; films of graphene; thin metal films; inherently conductive polymers (ICPs); aluminum zinc oxide (AZO), gallium zinc oxide (GZO) or indium zinc oxide (IZO).

The apparatus 100 comprises, in an example embodiment, a flexible printed circuit (FPC) configured to operatively connect the sensor 102 to the driver 106. The flexible printed circuit can be used to enable hinging of the frame 101 as with normal eyeglasses. In an alternative embodiment, the apparatus 100 comprises a printed wiring board (PWB) configured to operatively connect the sensor 102 to the driver 104. In such an embodiment, the frame 101 is not hinged or the driver 104 can be so located that the frame 101 can be normally hinged. For instance, the driver 104 can reside at a lower or upper portion of a frame surrounding the lens 104 or in the middle part of the frame 101 bridging the left and right lenses over the nose 114 of the user 110.

The apparatus 100 of FIGS. 1 and 2 comprises an analog-to-digital converter configured to convert analog signals produced by the sensor 102 to digital signals. The analog-to-digital converter is embodied in an example embodiment in the driver 106. Alternatively, in other example embodiments, the analog-to-digital converter resides on the flexible printed circuit may comprise the driver or on the printed wiring board. The driver can also be either separated or combined with the flexible printed circuit or with the printed wiring board.

In an example embodiment, the apparatus 100 further comprises a touch controller for detecting touching of the user at one or more touch sensitive areas of the apparatus 100. The touch sensitive areas are provided in the body and/or on the driver. Thus, the user can be allowed to provide commands or information by touching one or more parts of the apparatus 100. In an example embodiment, the commands in question can be restricted to merely one command such as power on or power off. In other example embodiments, the commands may relate to controls of an application running in the apparatus 100 or at an external device.

In an example embodiment, the apparatus 100 further comprises a heartbeat detector 108. In an example embodiment and in FIG. 2, the heartbeat detector is integrated with or attached to the body. The heartbeat detector is shown in FIG. 2 arranged behind an ear of the user when the apparatus is worn by the user.

In an example embodiment and in FIG. 2, the body 101 is configured to support the transparent capacitive sensor 102 in front of the eye 112 of the user 110 at a proximate distance. The proximate distance is, for instance, such that the eyelash of the user does not reach to transparent materials in front of the eye. The proximate distance can also be that long that the eyebrow of the user does not reach to transparent materials in the visible field of the eye. In an example embodiment and in FIG. 2, the proximate distance corresponds to the distance of normal eyeglass lenses from the eyes 112 of the user 110.

In an example embodiment and in FIGS. 1 and 2, the apparatus 100 comprises two of the sensors 102. The apparatus 100 is then configured support one of the sensors in front of each of two eyes of the user. In an alternative two-eye implementation, the apparatus has one extended sensor that extends over both eyes of the user.

For communicating with external devices, the apparatus has a connection interface in some example embodiments. Then, the apparatus can provide the external device with eye tracking signals corresponding to the detected eye movements. The apparatus can also be configured to provide the external device with eye tracking signals corresponding to other sensory data collected by the apparatus, such as heartbeat information or touch information.

In an example embodiment, the communication interface comprises a wired connection interface. The wired connection interface is, for example, compliant with a standard, such as Inter-Integrated Circuit (I2C) protocol, Serial Peripheral Interface (SPI), Universal serial bus (USB) or IEEE-1394.

In an example embodiment, the apparatus is configured to receive operating power from the external device. The power can be received through the wired communication interface. For instance, USB and IEEE-1394 readily provide for power transfer simultaneously with data transfer.

In an example embodiment, the communication interface comprises a wireless connection interface. The wireless connection interface is, for instance, compliant with a standard such as low power Bluetooth, IEEE 802.11 (wireless LAN), ultra-wide band (UWB) radio link or Infrared Data Association (IrDA) link.

Figure 5:
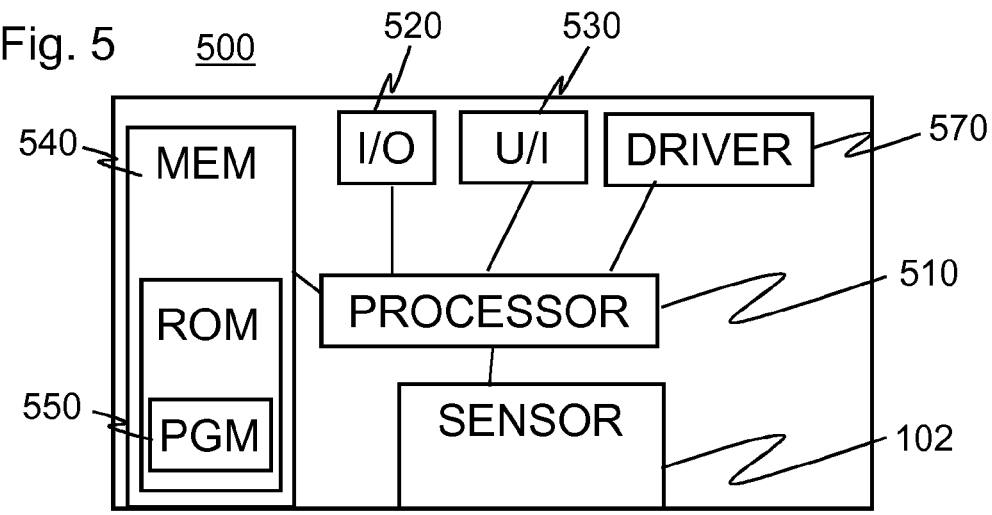

The apparatus 100 or an external device communicatively connectable with the apparatus (wirelessly or with wires) comprises in an example embodiment a controller 500 configured to use eye tracking information produced by the apparatus 100 for controlling an application, function of a controllable entity or a service accordingly. FIG. 5 shows an example embodiment of equipment suited for illustration of the controller. FIG. 5 can also be suited for illustration of the driver according to some example embodiments.

The device 500 comprises a communication interface 520, a processor 510 coupled to the communication interface module 520, and a memory 540 coupled to the processor 510. The memory 540 comprises a work memory and a non-volatile memory such as a read-only memory, flash memory, optical or magnetic memory. In the memory 540, typically at least initially in the non-volatile memory, there is stored software 550 operable to be loaded into and executed by the processor 510. The software 550 may comprise one or more software modules and can be in the form of a computer program product that is software stored in a memory medium. The device 500 further comprises a sensor 102 and a driver 570 each coupled to the processor (when exemplifying the apparatus 100, but not necessarily when exemplifying an external device).

It shall be understood that any coupling in this document refers to functional or operational coupling; there may be intervening components or circuitries in between coupled elements.

The communication interface module 520 is configured to provide local communications over one or more local links. The links may be wired and/or wireless links. The communication interface 520 may further or alternatively implement telecommunication links suited for establishing links with other users or for data transfer (e.g. using the Internet). Such telecommunication links may be links using any of: wireless local area network links, Bluetooth, ultra-wideband, cellular or satellite communication links. The communication interface 520 may be integrated into the device 500 or into an adapter, card or the like that may be inserted into a suitable slot or port of the device 500. While FIG. 5 shows one communication interface 520, the device may comprise a plurality of communication interfaces 520.

The processor 510 is, for instance, a central processing unit (CPU), a microprocessor, a digital signal processor (DSP), a graphics processing unit, an application specific integrated circuit (ASIC), a field programmable gate array, a microcontroller or a combination of such elements. FIG. 5 shows one processor 510, but the device 500 may comprise a plurality of processors.

As mentioned in the foregoing, the memory 540 may comprise volatile and a non-volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. In some example embodiments, only volatile or non-volatile memory is present in the device 500. Moreover, in some example embodiments, the device comprises a plurality of memories. In some example embodiments, various elements are integrated. For instance, the memory 540 can be constructed as a part of the device 500 or inserted into a slot, port, or the like. Further still, the memory 540 may serve the sole purpose of storing data, or it may be constructed as a part of an apparatus serving other purposes, such as processing data. Similar options are thinkable also for various other elements.

A skilled person appreciates that in addition to the elements shown in FIG. 5, the device 500 may comprise other elements, such as microphones, displays, as well as additional circuitry such as further input/output (I/O) circuitries, memory chips, application-specific integrated circuits (ASIC), processing circuitry for specific purposes such as source coding/decoding circuitry, channel coding/decoding circuitry, ciphering/deciphering circuitry, and the like. Additionally, the device 500 may comprise a disposable or rechargeable battery (not shown) for powering the device when external power if external power supply is not available.

Figure 6:
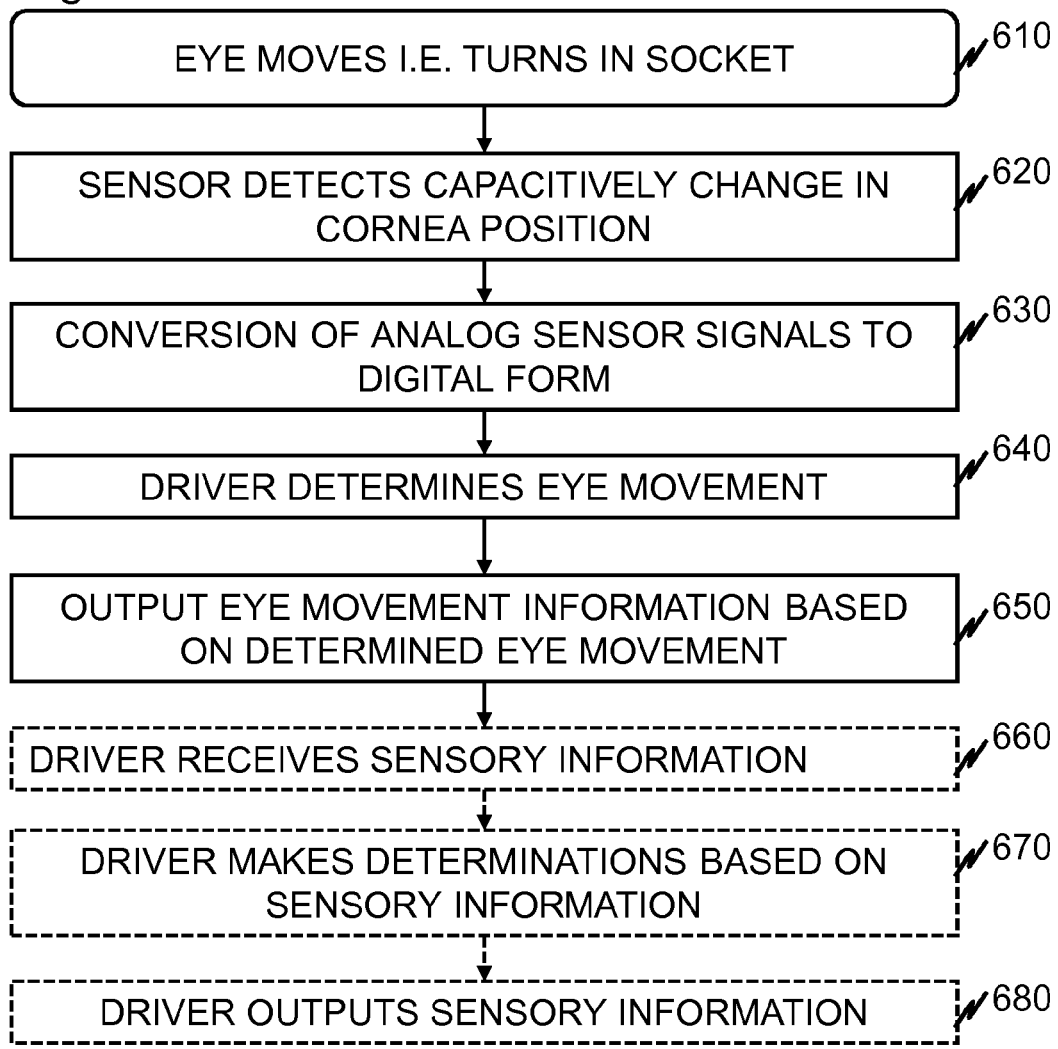
FIG. 6 shows a schematic flow chart illustrating a process according to an example embodiment.

FIG. 6 shows a schematic flow chart illustrating a process according to an example embodiment.

In step 610, the eye 112 moves i.e. turns in its socket so that the bulging cornea moves with respect to the sensor 102. In response, the sensor 102 detects 620 a change in the position of the cornea and produces respective or respectively changed analogue signals to the driver 104. The driver or an intervening analogue-to-digital converter converts 630 the analogue signals into digital form. Armed with the digital signals, the driver 106 determines 640 how the eye 112 has moved and outputs 650 corresponding eye tracking information. The driver 106 or another entity of the apparatus 100 can also receive 660 other sensory information such as heartbeat sensor information, microphone signals and/or touch sensor information. In response, the driver 106 makes sensory determinations 670 such as determination of pulse of the user, surrounding noise (clapping of hands sensory determination information is output 680 for use of the controller 500, for instance.

The eye tracking information is used according to different example embodiments various uses such as:
1. Activity Recognition
2. Advertising studies
3. Cognitive Studies
4. Communication systems for disabled
5. Computer usability studies
6. Enriched image and video communications where eye movements indicate feelings or reactions
7. Fatigue Detection
8. Geriatric Research
9. In-vehicle Research
10. Medical Research
11. Training Simulators
12. Vehicle Simulators
13. Virtual Reality Without in any way limiting the scope, interpretation, or application of the claims appearing below, a technical effect of one or more of the example embodiments disclosed herein is that the eyes of a user can be tracked with contactless arrangement. Another technical effect of one or more of the example embodiments disclosed herein is that the contactless arrangement can be portable. Another technical effect of one or more of the example embodiments disclosed herein is that further sensory determinations can be made in conjunction with eye tracking.

Embodiments of the present invention may be implemented in software, hardware, application logic or a combination of software, hardware and application logic. The software, application logic and/or hardware may reside on a driver and/or on an external device communicatively connected with the driver. In an example embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with an example of a computer described and depicted in FIG. 5. A computer-readable medium may comprise a computer-readable storage medium that may be any media or means that can contain or store the instructions for use by or in connection with an instruction execution system, apparatus, or device, such as a computer.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications which may be made without departing from the scope of the present invention as defined in the appended claims.

What is claimed is:

1. An apparatus, comprising:
a transparent capacitive sensor;
a body configured to support the transparent capacitive sensor in front of an eye of a user; and
a driver configured to receive signals from the sensor and to determine eye movements based on the received signals.

2. The apparatus of claim 1, wherein the sensor is configured to detect movement of the eye based on electrostatic effect caused by a bulge of eye cornea.

3. The apparatus of claim 1, wherein the apparatus is wearable by the user.

4. The apparatus of claim 1, wherein the apparatus is wearable as eyeglasses.

5. The apparatus of claim 1, wherein the apparatus comprises a display configured to enable the apparatus to be worn as video glasses.

6. The apparatus of claim 5, wherein the sensor is attached to the display.

7. The apparatus of claim 1, wherein the sensor comprises two layers of transparent conductive material sandwiching a layer of non-conductive material.

8. The apparatus of claim 1, wherein the sensor is integrated with a lens of eyeglasses.

9. The apparatus of claim 1, further comprising a touch controller.

10. The apparatus of claim 9, wherein the touch controller is configured to detect touching of the user at one or more touch sensitive areas in the body and/or on the driver.

11. The apparatus of claim 1, further comprising a heartbeat detector.

12. The apparatus of claim 11, wherein the heartbeat detector is integrated with or attached to the body.

13. The apparatus of claim 1, further comprising a wireless connection interface for connecting with an external device.

14. A method comprising:
supporting a transparent capacitive sensor in front of an eye of a user;
sensing movement of the eye of the user by the transparent capacitive sensor and producing corresponding signals; and
determining eye movements based on the produced signals.

15. The method of claim 14, wherein the sensor is configured to detect movement of the eye based on electrostatic effect caused by a bulge of eye cornea.

16. The method of claim 14, wherein the apparatus is wearable by the user.

17. The method of claim 14, further comprising detecting touching of the user at one or more touch sensitive elements.

18. The method of claim 17, further comprising carrying by a common body the transparent capacitive sensor and the one or more touch sensitive elements.

19. The method of claim 14, further comprising detecting heartbeat of the user.

20. A method comprising:
    receiving signals from a transparent capacitive sensor located in front of an eye of a user; and
    determining movement of the eye based on the received signals.

21. A non-transitory memory medium comprising a computer program that comprises:
    code for receiving signals from a transparent capacitive sensor located in front of an eye of a user; and
    code for determining movement of the eye based on the received signal;
    when the computer program is run on a processor.

* * * * *